(12) United States Patent
Young (10) Patent No.: US 9,941,034 B2
(45) Date of Patent: Apr. 10, 2018

(54) DIRECT WRITE DISPENSING APPARATUS AND METHOD

(71) Applicant: HONEYWELL FEDERAL MANUFACTURING & TECHNOLOGIES, LLC, Kansas City, MO (US)

(72) Inventor: Barbara Young, Raymore, MO (US)

(73) Assignee: Honeywell Federal Manufacturing & Technologies, LLC, Kansas City, MO (US)

( * ) Notice: Subject to any disclaimer, the term of this patent is extended or adjusted under 35 U.S.C. 154(b) by 0 days.

(21) Appl. No.: 15/151,165

(22) Filed: May 10, 2016

(65) Prior Publication Data

US 2017/0330654 A1    Nov. 16, 2017

(51) Int. Cl.
*H01B 13/02* (2006.01)
*B05D 1/02* (2006.01)
(Continued)

(52) U.S. Cl.
CPC ........... *H01B 13/0271* (2013.01); *A61K 9/00* (2013.01); *A61K 38/00* (2013.01); *A61K 47/00* (2013.01); *B05D 1/02* (2013.01); *D01D 5/00* (2013.01); *D04H 1/00* (2013.01); *G03G 15/00* (2013.01); *H01B 13/0003* (2013.01); *H01B 13/06* (2013.01)

(58) Field of Classification Search
CPC . D01D 5/00; D04H 1/00; G03G 15/00; A61K 38/00; A61K 47/00; A61K 9/00; Y10T 428/00; Y10T 442/00
See application file for complete search history.

(56) References Cited

U.S. PATENT DOCUMENTS

| 3,423,489 A | 1/1969 | Arens et al. |
| 4,372,648 A | 2/1983 | Black |
(Continued)

FOREIGN PATENT DOCUMENTS

WO    WO2014200595    12/2014

OTHER PUBLICATIONS

"Core-Shell Nanofibers: Nano Channel and Capsule by Coaxial Electrospinning", Fengyu Li, Yong Zhao and Yanlin Song, Nanofibers, chapter 22, pp. 419-438, Pub by INTECH, 2010.*

(Continued)

*Primary Examiner* — David P Turocy
*Assistant Examiner* — Mohammad Mayy
(74) *Attorney, Agent, or Firm* — Hovey Williams LLP (57) ABSTRACT

A direct write dispensing nozzle assembly and method of forming traces and twisted pairs via direct write dispensing. The method includes dispensing conductive material via an inner nozzle so as to form a conductive core. Non-conductive material may be dispensed via a peripheral nozzle surrounding the inner nozzle so as to form a non-conductive casing surrounding the conductive core. The first conductive core and the non-conductive casing may then be deposited on a substrate or other surface. The trace may be positioned on the substrate such that the non-conductive casing contacts a previously deposited trace. An additional conductive core may be dispensed within the non-conductive casing and the direct write dispensing nozzle assembly may be rotated so as to form a twisted pair.

10 Claims, 4 Drawing Sheets

(51) Int. Cl.
*H01B 13/06* (2006.01)
*H01B 13/00* (2006.01)
*A61K 47/00* (2006.01)
*D04H 1/00* (2006.01)
*D01D 5/00* (2006.01)
*A61K 9/00* (2006.01)
*G03G 15/00* (2006.01)
*A61K 38/00* (2006.01)

(56) References Cited

U.S. PATENT DOCUMENTS

| | | | |
|---|---|---|---|
| 4,643,854 | A | 2/1987 | Kendall, Jr. et al. |
| 7,317,196 | B2 | 1/2008 | Partlo et al. |
| 7,972,650 | B1 | 7/2011 | Church et al. |
| 8,261,662 | B1 | 9/2012 | Shile et al. |
| 8,435,477 | B2 | 5/2013 | Kambe et al. |
| 8,568,684 | B2 | 10/2013 | Bi et al. |
| 8,640,975 | B2 | 2/2014 | King |
| 2009/0053507 | A1 | 2/2009 | Hoey et al. |
| 2010/0148404 | A1* | 6/2010 | Smida ............... D01D 5/0069 264/465 |
| 2010/0203315 | A1* | 8/2010 | Barrero Ripoll ......... B32B 3/12 428/293.1 |
| 2011/0068493 | A1* | 3/2011 | Buyuktanir ...... B29D 11/00663 264/1.27 |
| 2012/0082744 | A1* | 4/2012 | Jo ....................... D01D 5/0069 425/149 |
| 2014/0035177 | A1* | 2/2014 | Lipton .................... D01D 5/18 264/8 |

OTHER PUBLICATIONS

"Manipulation on the Morphology and Electrical Properties of Aligned Electrospun Nanofibers of Poly(3-hexylthiophene) for Field-Effect Transistor Applications", Jung-Yao Chen, Chi-Ching Kuo, Chia-Sheng Lai, Wen-Chang Chen, and Hsin-Lung Chen, Macromolecules, 2011, 44, 2883-2892.*

Orme et al., "Charged Molten Metal Droplet Deposition as a Direct Write Technology," MRS 2000 Spring Meeting, San Francisco, Apr. 2000.

Folgar et al., "Multifunctional Material Direct Printing for Laser Sintering Systems," International Solid Freeform Fabrication Symposium, 2013.

Rivas-Cardona et al., "Microfluidic Device for Delivery of Multiple Inks for Dip Pen Nanolithography," J. Micro/Nanolith. MEMS MOEMS 6(3), 033004, Jul.-Sep. 2007.

* cited by examiner

DIRECT WRITE DISPENSING APPARATUS AND METHOD

BACKGROUND

Direct write dispensing is often used for forming increasingly small and complex conductive traces for microelectronics. However, the smaller scale and greater complexity increases the likelihood of the traces shorting with nearby traces. Signals traveling through the traces are also more likely to be affected by noise and interference from signals traveling through nearby traces. Conventional direct write dispensing requires pattern restrictions and/or additional steps to ensure that the traces are sufficiently separated from each other or sufficiently insulated from each other. This limits the complexity and miniaturization of the traces and increases the amount of time and effort required to design the microelectronics.

SUMMARY

Embodiments of the present invention solve the above-mentioned problems and provide a distinct advance in the art of direct write dispensing. More particularly, the present invention provides a direct write dispensing nozzle assembly and a method for direct write dispensing traces adjacent to each other without shorting and with minimal signal interference therebetween.

An embodiment of the invention is a method of forming a trace via direct write dispensing. The method includes dispensing conductive material via an inner nozzle so as to form a conductive core. Non-conductive material is dispensed via a peripheral nozzle surrounding the inner nozzle so as to form a non-conductive casing surrounding the conductive core. The first conductive core and the non-conductive casing is then deposited on a substrate or other surface. The trace is positioned on the substrate such that the non-conductive casing contacts a previously deposited trace. In this way, traces may be quickly and easily formed such that the conductive cores of adjacent traces do not short together.

Another embodiment of the invention is a method of forming an electronic twisted pair via direct write dispensing. The method includes dispensing conductive material via a first inner nozzle so as to form a first conductive core. Conductive material is dispensed via a second inner nozzle spaced from the first inner nozzle so as to form a second conductive core spaced from the first conductive core. Non-conductive material is dispensed via a peripheral nozzle so as to form a non-conductive casing surrounding the conductive cores. The inner nozzles and the peripheral nozzle may be rotated about a longitudinal axis so that the first conductive core and the second conductive core form a double helix. The first inner nozzle, the second inner nozzle, and the peripheral nozzle may be independently opened and closed and rotation of the direct write dispensing nozzle assembly may be independently controlled so as to effect a number of helix variations and modifications.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the preferred embodiments and the accompanying drawing figures.

BRIEF DESCRIPTION OF THE DRAWINGS

Embodiments of the present invention are described in detail below with reference to the attached drawing figures, wherein.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention may be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Figures 1, 2:
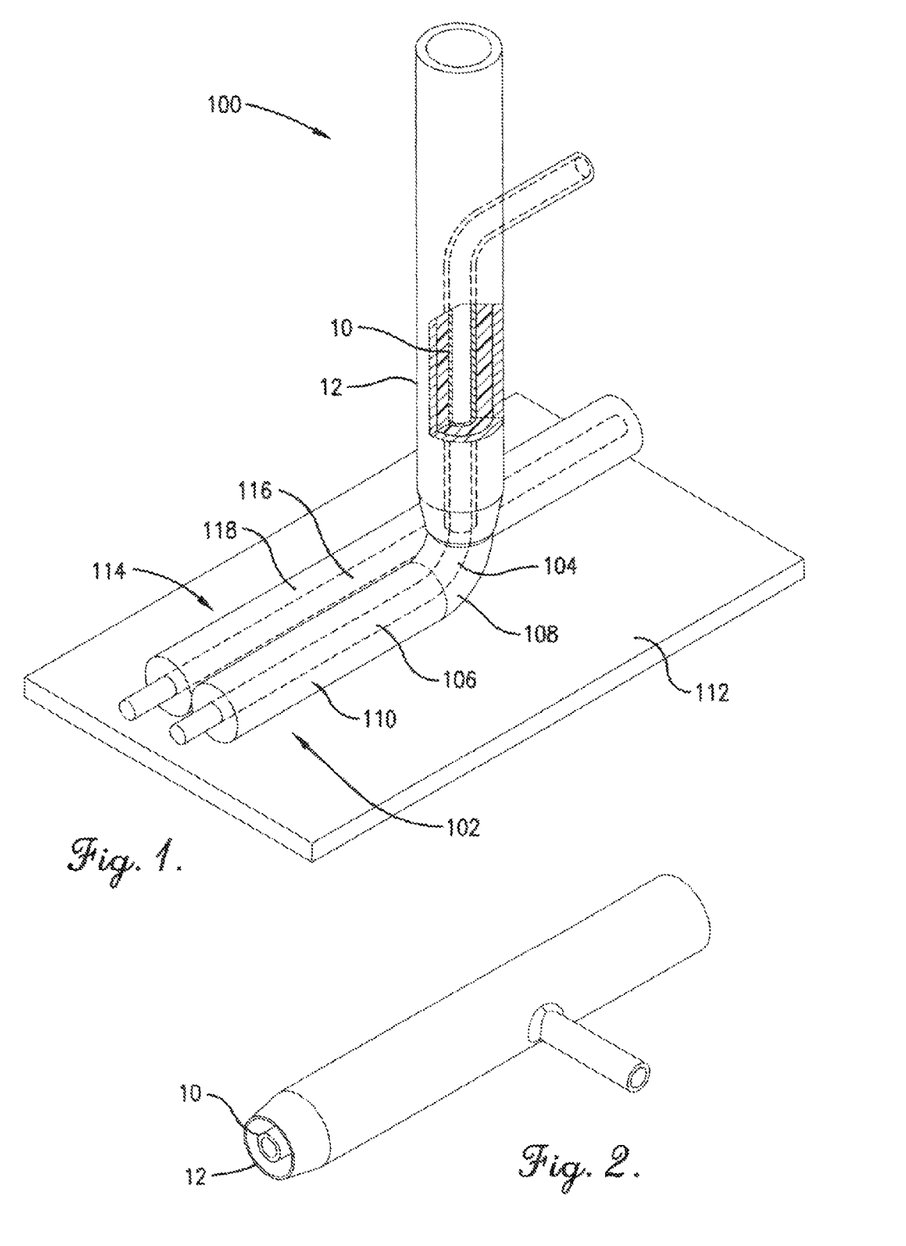
FIG. 1 is a perspective view of a direct write dispensing nozzle assembly constructed in accordance with an embodiment of the present invention.
FIG. 2 is an end perspective view of the direct write dispensing nozzle assembly of FIG. 1.

Turning to FIGS. 1 and 2, a direct write dispensing nozzle assembly 100 constructed in accordance with an embodiment of the present invention is illustrated. The direct write dispensing nozzle assembly 100 may be used for dispensing traces adjacent to each other on a substrate or other electronic component and broadly comprises an inner nozzle 10 and a peripheral nozzle 12 for creating a trace 102 of an electronic circuit.

The inner nozzle 10 dispenses conductive material 104 for forming a conductive core 106 of the trace 102 and may be an open-ended conduit. The inner nozzle 10 may be circular, elongated, slot-like, or any other suitable shape such that the conductive core 106 takes the shape of the inner nozzle 10. The inner nozzle 10 may also taper inwardly or flare outwardly near its open end for improving the dispensing of conductive material 104. The inner nozzle 10 may be selectively and reversibly closeable and/or redirectable. For example, the inner nozzle 10 may be opened to begin creating the conductive core 106 and closed to terminate the conductive core 106. The inner nozzle 10 may also be angled, rotated, pivoted, or translated to create essentially any desirable trace path.

The peripheral nozzle 12 dispenses non-conductive material 108 for forming a non-conductive casing 110 of the trace 102 and may be an open-ended conduit at least partially enclosing or surrounding the inner nozzle 10. The peripheral nozzle 12 may be circular, elongated, slot-like, or any other suitable shape such that the non-conductive casing 110 takes the shape of the peripheral nozzle 12. The peripheral nozzle 12 may be concentric with the inner nozzle 10 such that the non-conductive casing 110 has a uniform thickness around the conductive core 106. The peripheral nozzle 12 may also taper inwardly or flare outwardly near its open end for improving of non-conductive material 108 and for conforming to the shape of the inner nozzle 10. The peripheral nozzle 12 may be selectively and reversibly closeable and/or redirectable. For example, the peripheral nozzle 12 may be opened to begin creating the non-conductive casing 110 and closed to terminate the non-conductive casing 110.

Use of the direct write dispensing nozzle assembly 100 will now be described in more detail. First, the direct write dispensing nozzle assembly 100 may be positioned near a substrate 112 such as a ceramic circuit board substrate, as shown in block 200 of FIG. 3. To that end, the direct write dispensing nozzle assembly 100 may be actuated or manually shifted towards the substrate 112. Alternatively, the substrate 112 may be brought into close proximity to the direct write dispensing nozzle assembly 100.

Figure 3:
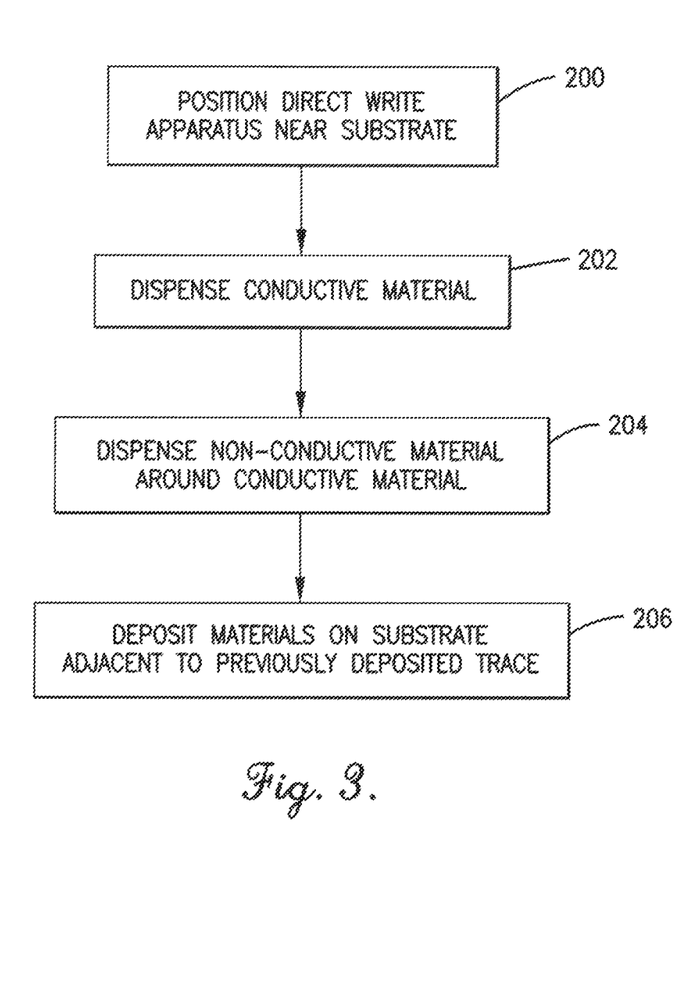
FIG. 3 is a flow diagram of steps in a method of creating a trace via the direct write dispensing nozzle assembly of FIG. 1.

The inner nozzle 10 may then begin dispensing conductive material 104 so as to form the conductive core 106, as shown in block 202. The inner nozzle 10 may initially direct the conductive material 104 into contact with electronic contacts, buses, or other electronic components of the substrate 112 for beginning or continuing portions of an electronic circuit. To that end, the inner nozzle 10 may be selectively opened when the nozzle assembly 100 is in a desired beginning position.

The peripheral nozzle 12 may also begin dispensing non-conductive material 108 so as to form the non-conductive casing 110 at least partially surrounding, enclosing, encasing, or enveloping the conductive core 106, as shown in block 204. The peripheral nozzle 12 may begin dispensing non-conductive material 108 before, after, or at the same time the inner nozzle 10 begins dispensing conductive material 104. In this way, a first end of the conductive core 106 may extend beyond, even with, or short of a first end of the non-conductive casing.

The inner nozzle 10 and the peripheral nozzle 12 may deposit the conductive material 104 and the non-conductive material 110 so that the non-conductive casing 110 contacts the substrate 112 adjacent to a previously deposited trace 114, as shown in block 206. More specifically, the conductive core 106 may be spaced from a conductive core 116 of the previously deposited trace 114 while the non-conductive casing 110 contacts a non-conductive casing 118 of the previously deposited trace 114.

The inner nozzle 10 may then discontinue dispensing conductive material 104 so as to terminate the conductive core 106, as shown in block 208. The inner nozzle 10 may direct the conductive material 104 into contact with electronic contacts, buses, or other electronic components of the substrate 112 for completing portions of the electronic circuit. To that end, the inner nozzle 10 may be selectively closed when the nozzle assembly 100 is in a desired finishing position.

The peripheral nozzle 12 may also discontinue dispensing non-conductive material 108 so as to terminate the non-conductive casing 110, as shown in block 210. The peripheral nozzle 12 may discontinue dispensing non-conductive material 108 before, after, or at the same time the inner nozzle 10 discontinues dispensing conductive material 104. In this way, a second end of the conductive core 106 may extend beyond, even with, or short of a second end of the non-conductive casing.

The above-described nozzle assembly 100 and method of direct write depositing provides several advantages over conventional nozzles and methods. For example, direct write depositing via the nozzle assembly 100 optimizes space on the substrate 112 while preventing the conductive cores 106, 116 from shorting between each other or causing unwanted interference therebetween. The amount of conductive material 104 and non-conductive material 108 used to create the conductive core 106 and the non-conductive casing 110 can be controlled by opening and closing the inner nozzle 10 and the peripheral nozzle 12. The trace 102 can be made to follow trace paths having complicated shapes, patterns, and lengths by computer control of the nozzle assembly 100. The inner nozzle 10 and the peripheral nozzle 12 may be independently controlled so that the conductive core 106 and the non-conductive casing 110 may begin and terminate at different points. This may be particularly useful for creating core leads and other circuit components.

Figures 4, 5:
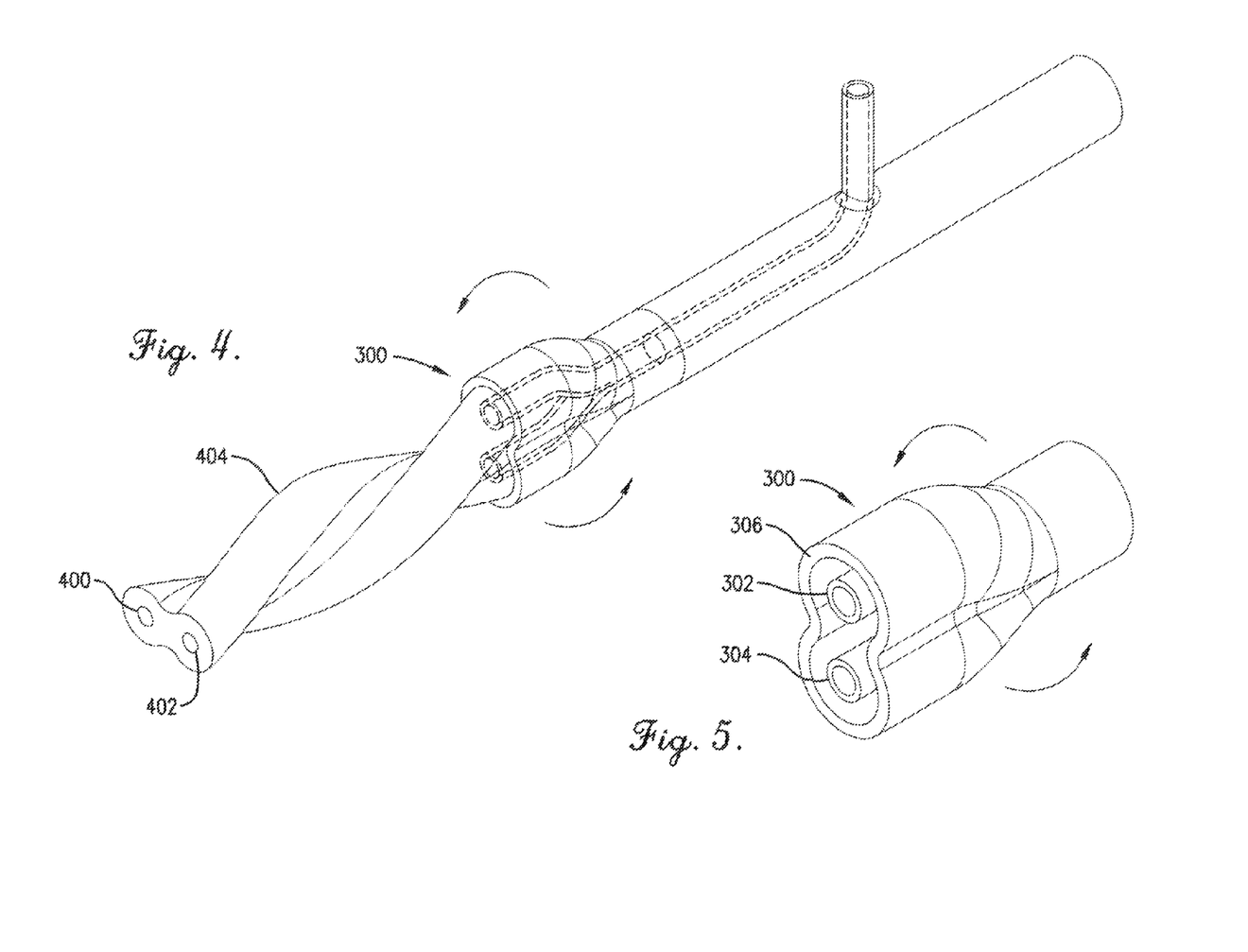
FIG. 4 is a perspective view of a direct write twisted pair nozzle assembly constructed in accordance with another embodiment of the present invention.
FIG. 5 is an end perspective view of the direct write twisted pair nozzle assembly of FIG. 4.

A direct write twisted pair nozzle assembly 300 constructed in accordance with another embodiment of the present invention is illustrated in FIGS. 4 and 5. The direct write twisted pair nozzle assembly 300 broadly comprises a first inner nozzle 302, a second inner nozzle 304, and a peripheral nozzle 306.

The first inner nozzle 302 dispenses conductive material for forming a first conductive core 400 and may be an open-ended conduit. The first inner nozzle 302 may be circular, elongated, slot-like, or any other suitable shape such that the first conductive core 400 takes the shape of the first inner nozzle 302. The first inner nozzle 302 may also taper inwardly or flare outwardly near its open end for improving the dispensing of conductive material. The first inner nozzle 302 may be selectively and reversibly closeable and/or redirectable. For example, the first inner nozzle 302 may be opened to begin creating the first conductive core 400 and closed to terminate the first conductive core 400. The first inner nozzle 302 may also be angled, rotated, pivoted, or translated to create essentially any desirable electronic wire, as described in more detail below.

The second inner nozzle 304 dispenses conductive material and may be an open-ended conduit spaced from the first inner nozzle 302 for forming a second conductive core 402 spaced from the first conductive core 400. The second inner nozzle 304 may be circular, elongated, slot-like, or any other suitable shape such that the second conductive core 402 takes the shape of the second inner nozzle 304. The second inner nozzle 304 may also taper inwardly or flare outwardly near its open end for improving the dispensing action of the second inner nozzle 304. The second inner nozzle 304 may be conjoined with the first inner nozzle 302 at their upstream ends so that the first inner nozzle 302 and the second inner nozzle 304 receive conductive material from a common source. The second inner nozzle 304 may be selectively and reversibly closeable and/or redirectable. For example, the second inner nozzle 304 may be opened to begin creating the second conductive core 402 and closed to terminate the second conductive core 402. The second inner nozzle 304 may also be angled, rotated, pivoted, or translated to create essentially any desirable electronic wire, as described in more detail below. The second inner nozzle 304 may be controlled independently from the first inner nozzle 302.

The peripheral nozzle 306 dispenses non-conductive material for forming a non-conductive casing 404 and may be an open-ended conduit at least partially enclosing or surrounding the inner nozzles 302, 304. The peripheral nozzle 306 may be circular, elongated, slot-like, "figure-8" shaped or any other suitable shape such that the non-conductive casing 404 takes the shape of the peripheral nozzle 306. A portion of the peripheral nozzle 306 may be concentric with the first inner nozzle 302 while another portion of the peripheral nozzle 306 may be concentric with the second inner nozzle 304 such that the non-conductive casing 404 has a uniform thickness around portions of the conductive cores 400, 402. The peripheral nozzle 306 may also taper inwardly or flare outwardly near its open end for improving dispensing of non-conductive material and for conforming to the shapes of the inner nozzles 302, 304. The peripheral nozzle 306 may be selectively and reversibly closeable and/or redirectable. For example, the peripheral nozzle 306 may be opened to begin creating the non-conductive casing 404 and closed to terminate the non-conductive casing 404. The peripheral nozzle 306 may also be controlled independently from the first inner nozzle 302 and/or the second inner nozzle 304.

Use of the direct write twisted pair nozzle assembly 300 will now be described in more detail. First, the first inner nozzle 302 and the second inner nozzle 304 may dispense conductive material so as to form the first conductive core 400 and the second conductive core 402 spaced from the first conductive core 400, as shown in block 500 of FIG. 6. The first inner nozzle 302 and the second inner nozzle 304 may begin dispensing the conductive material simultaneously or independently from each other.

Figure 6:
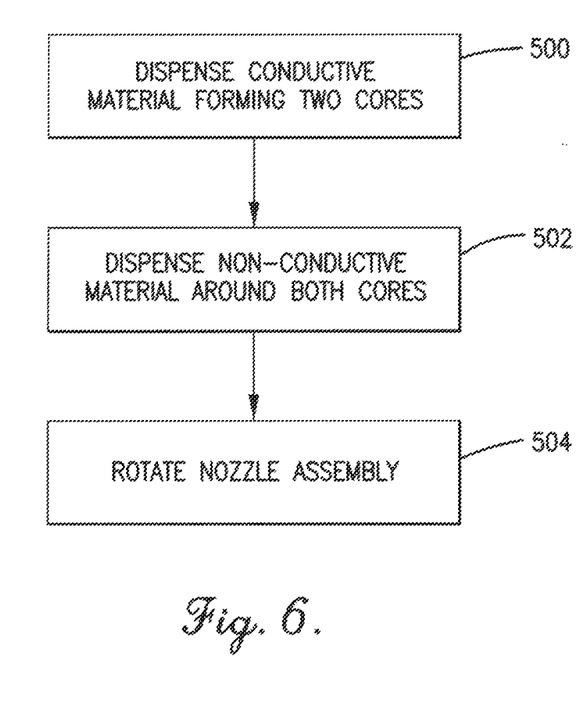
FIG. 6 is a flow diagram of steps in a method of creating a twisted pair via the direct write twisted pair nozzle assembly of FIG. 4.

The peripheral nozzle 306 may also dispense non-conductive material such that the non-conductive material at least partially surrounds, encloses, or encases the conductive cores 400, 402, as shown in block 502. The non-conductive material may also be dispensed between the conductive cores 400, 402 to electrically isolate the conductive cores 400, 402 from each other. The peripheral nozzle 306 may begin dispensing the non-conductive material before, after, or the same time that the first inner nozzle 302 and/or the second inner nozzle 304 begin dispensing the conductive material.

The direct write twisted pair nozzle assembly 300 may be rotated while the conductive cores 400, 402 and the non-conductive casing 404 are being formed such that the conductive cores 400, 402 twist about each other so as to form a double helix, as shown in block 504. Distal ends of the conductive cores 400, 402, and/or the non-conductive casing 404 may need to be anchored or fixed so that the rotation of the twisted pair nozzle assembly 300 twists the conductive cores 400, 402.

The above-described direct write twisted pair nozzle assembly 300 and method of forming a twisted pair provide several advantages over conventional nozzles and methods. For example, formation of the conductive cores 400, 402 and non-conductive casing 404 can be independently controlled so that complex twisted pairs can be created. The speed at which the conductive material and non-conductive material are dispensed and the rate of rotation can be controlled to create twisted pairs having tight or loose helixes and even helixes of varying periods.

Figures 7, 8:
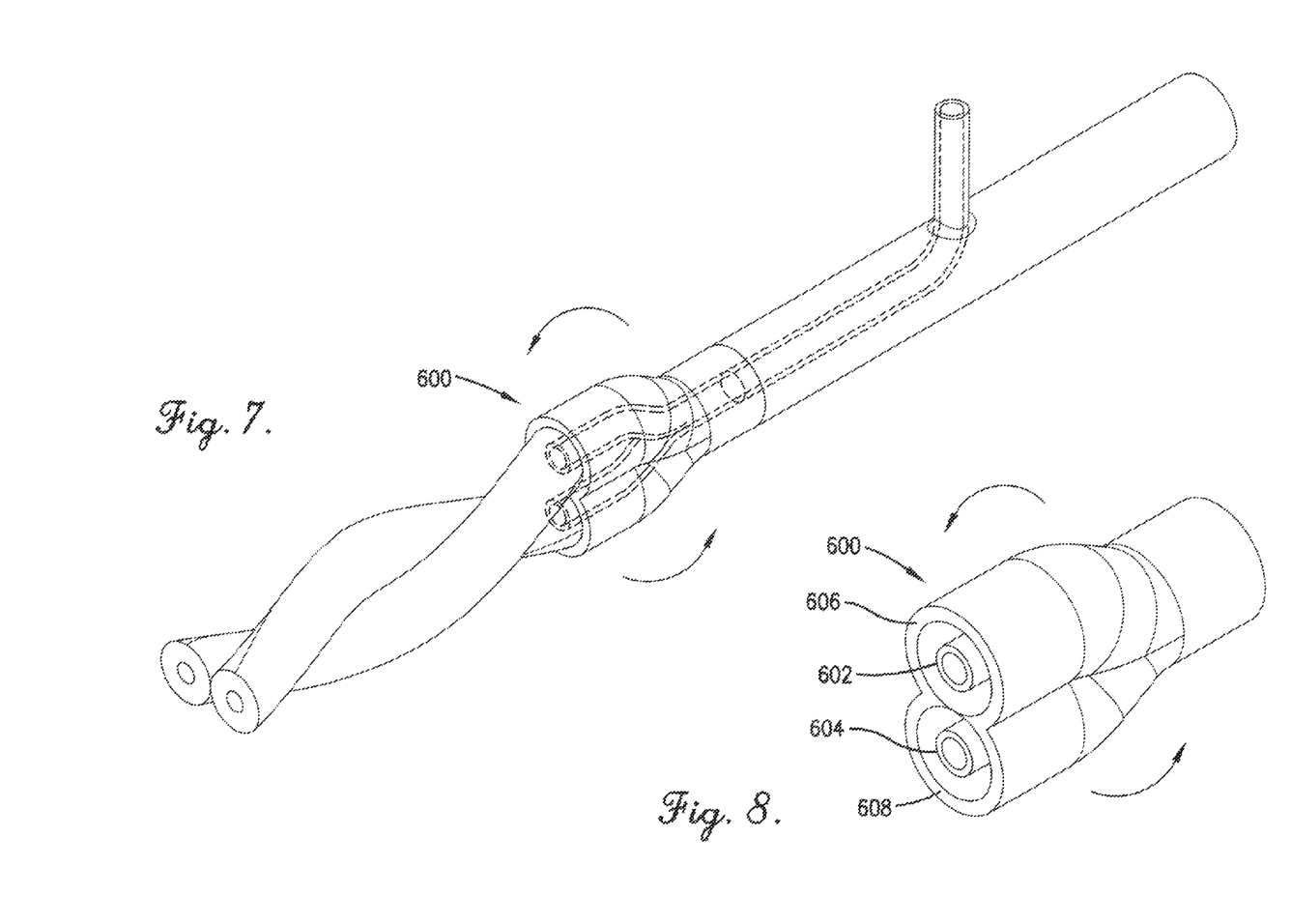
FIG. 7 is a perspective view of a direct write twisted pair nozzle assembly constructed in accordance with yet another embodiment of the present invention.
FIG. 8 is an end perspective view of the direct write twisted pair nozzle assembly of FIG. 7.

A direct write twisted pair nozzle assembly 600 constructed in accordance with yet another embodiment of the present invention is similar to the direct write twisted pair nozzle assembly 300 except the direct write twisted pair nozzle assembly 600 includes a first inner nozzle 602, a second inner nozzle 604, a first peripheral nozzle 606, and a second peripheral nozzle 608, as shown in FIGS. 7 and 8. The first inner nozzle 602 and the second inner nozzle 604 are similar to the inner nozzles 302, 304 described above and form the first and second conductive cores 700, 702.

The first peripheral nozzle 606 is similar to the peripheral nozzle 306 except the first peripheral nozzle 606 may be an open-ended conduit at least partially enclosing or surrounding the first inner nozzle 602 but not the second inner nozzle 604 for forming a first non-conductive casing 704. The first peripheral nozzle 606 may be circular, elongated, slot-like, or any other suitable shape. The first peripheral nozzle 606 may be concentric with the first inner nozzle 602. The first peripheral nozzle 606 may also taper inwardly or flare outwardly near its open end for improving the dispensing of non-conductive material and for conforming to the shape of the first inner nozzle 602. The first peripheral nozzle 606 may be selectively and reversibly closeable and/or redirectable. For example, the first peripheral nozzle 606 may be opened to begin creating the first non-conductive casing 704 and closed to terminate the first non-conductive casing 704.

The second peripheral nozzle 608 is similar to the first peripheral nozzle 606 except the second peripheral nozzle 608 may be an open-ended conduit at least partially enclosing or surrounding the second inner nozzle 604 but not the first inner nozzle 602. The second peripheral nozzle 608 may be adjacent to or spaced from the first peripheral nozzle 606 for forming a second non-conductive casing 706 adjacent to or spaced from the first non-conductive casing 704. The second peripheral nozzle 608 may be circular, elongated, slot-like, or any other suitable shape. The second peripheral nozzle 608 may be concentric with the second inner nozzle 604. The second peripheral nozzle 608 may also taper inwardly or flare outwardly near its open end for improving the dispensing action of the second peripheral nozzle 608 and for conforming to the shape of the second inner nozzle 604. The second peripheral nozzle 608 may be selectively and reversibly closeable and/or redirectable independently from the first peripheral nozzle 606. For example, the second peripheral nozzle 608 may be opened to begin creating the second non-conductive casing 706 and closed to terminate the second non-conductive casing 706.

The direct write twisted pair nozzle assembly 600 may form twisted pairs in substantially the same way as the direct write twisted pair nozzle assembly 300. That is, the direct write twisted pair nozzle assembly 600 may be rotated while the conductive cores 700, 702 and the non-conductive casings 704, 706 are being formed such that the conductive cores 700, 702 twist about each other and the non-conductive casings 704, 706 twist about each other so as to form a double helix.

It will be understood that aspects of the above-described direct write dispensing nozzle assembly 100 and the direct write twisted pair nozzle assemblies 300, 600, may be used together or in conjunction with each other. Similarly, steps for forming traces and twisted pairs via the dispensing nozzle assembly 100 and the direct write twisted pair nozzle assemblies 300, 600 may be used together or in conjunction with each other. For example, adjacent traces may be formed simultaneously and twisted via the direct write twisted pair nozzle assembly 300 while being deposited on a substrate.

Having thus described various embodiments of the invention, what is claimed as new and desired to be protected by Letters Patent includes the following:

1. A method of direct write dispensing an electronic twisted pair on a substrate, the method comprising the steps of:
   opening a first inner nozzle;
   dispensing conductive material via the first inner nozzle so as to form a first conductive core;
   opening a second inner nozzle independently from the first inner nozzle, the second inner nozzle being spaced from the first inner nozzle;
   dispensing conductive material via the second inner nozzle independently from dispensing the conductive material via the first inner nozzle so as to form a second conductive core spaced from the first conductive core independently from the first conductive core;
   opening a first peripheral nozzle independently from the first inner nozzle and second inner nozzle;
   dispensing non-conductive material via the first peripheral nozzle independently from dispensing the conductive material via the first inner nozzle and second inner nozzle so as to form a first non-conductive casing surrounding at least the first conductive core independently from the first conductive core and second conductive core; and
   rotating the first inner nozzle, the second inner nozzle, and the first peripheral nozzle near the substrate about a longitudinal axis independently from dispensing the conductive material and non-conductive material so that the first conductive core and the second conductive core cooperatively form double helix traces on the substrate.

2. The method of claim 1, wherein the first peripheral nozzle extends around the first inner nozzle and the second inner nozzle such that the first non-conductive casing surrounds the first conductive core and the second conductive core.

3. The method of claim 2, wherein the first inner nozzle and the second inner nozzle are circular.

4. The method of claim 3, wherein a portion of the peripheral nozzle is concentric around the first inner nozzle and another portion of the peripheral nozzle is concentric around the second inner nozzle.

5. The method of claim 1, further comprising the step of dispensing non-conductive material via a second peripheral nozzle so as to form a second non-conductive casing surrounding the second conductive core such that the first non-conductive casing contacts the second non-conductive casing, the step of rotating the first inner nozzle, the second inner nozzle, and the first peripheral nozzle includes rotating the second peripheral nozzle about the longitudinal axis.

6. The method of claim 5, wherein the first inner nozzle, the second inner nozzle, the first peripheral nozzle, and the second peripheral nozzle are circular, the first peripheral nozzle being concentric around the first inner nozzle and the second peripheral nozzle being concentric around the second peripheral nozzle.

7. The method of claim 1, wherein the longitudinal axis is halfway between the first inner nozzle and the second inner nozzle.

8. The method of claim 1, wherein the first inner nozzle, second inner nozzle, and first peripheral nozzle dispense material along axes extending parallel to the longitudinal axis of rotation.

9. A method of direct write dispensing an electronic twisted pair on a substrate, the method comprising the steps of:
   opening a first inner nozzle;
   dispensing conductive material via the first inner nozzle so as to form a first conductive core;
   opening a second inner nozzle independently from the first inner nozzle, the second inner nozzle being spaced from the first inner nozzle;
   dispensing conductive material via the second inner nozzle independently from dispensing the conductive material via the first inner nozzle so as to form a second conductive core spaced from the first conductive core independently from the first conductive core;
   opening a peripheral nozzle independently from the first inner nozzle and second inner nozzle;
   dispensing non-conductive material via the peripheral nozzle independently from dispensing the conductive material via the first inner nozzle and second inner nozzle so as to form a non-conductive casing surrounding the first conductive core and the second conductive core independently from the first conductive core and second conductive core, a portion of the peripheral nozzle being concentric with the first inner nozzle and another portion of the peripheral nozzle being concentric with the second inner nozzle; and
   rotating the first inner nozzle, the second inner nozzle, and the first peripheral nozzle near the substrate about a longitudinal axis independently from dispensing the conductive material and non-conductive material so that the first conductive core and the second conductive core cooperatively form double helix traces on the substrate.

10. The method of claim 9, wherein the first inner nozzle, second inner nozzle, and peripheral nozzle dispense material along axes extending parallel to the longitudinal axis of rotation.

\* \* \* \* \*

UNITED STATES PATENT AND TRADEMARK OFFICE
CERTIFICATE OF CORRECTION

PATENT NO. : 9,941,034 B2
APPLICATION NO. : 15/151165
DATED : April 10, 2018
INVENTOR(S) : Barbara Young

Page 1 of 1

It is certified that error appears in the above-identified patent and that said Letters Patent is hereby corrected as shown below:

In the Specification

Column 1, Line 20, add:
-- STATEMENT REGARDING FEDERALLY-SPONSORED RESEARCH OR DEVELOPMENT
This invention was made with government support under Contract No.: DE-NA0000622 awarded by the Department of Energy. The government has certain rights in the invention. --

Signed and Sealed this
Twenty-first Day of April, 2020

Andrei Iancu
*Director of the United States Patent and Trademark Office*